(12) United States Patent
Hawver et al.

(10) Patent No.: US 10,390,783 B2
(45) Date of Patent: Aug. 27, 2019

(54) DIGITAL RADIOGRAPHY DETECTOR IMAGE READOUT PROCESS

(71) Applicant: CARESTREAM HEALTH, INC., Rochester, NY (US)

(72) Inventors: Jeffery R. Hawver, Marion, NY (US); Gordon Geisbuesch, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 266 days.

(21) Appl. No.: 15/417,279

(22) Filed: Jan. 27, 2017

(65) Prior Publication Data

US 2017/0196523 A1     Jul. 13, 2017

Related U.S. Application Data

(63) Continuation of application No. 14/487,189, filed on Sep. 16, 2014, now Pat. No. 9,554,759.

(60) Provisional application No. 61/879,182, filed on Sep. 18, 2013.

(51) Int. Cl.
    *A61B 6/00*     (2006.01)
    *H04N 5/32*     (2006.01)

(52) U.S. Cl.
    CPC ............. *A61B 6/5205* (2013.01); *A61B 6/42* (2013.01); *A61B 6/4208* (2013.01); *A61B 6/4225* (2013.01); *A61B 6/4233* (2013.01); *A61B 6/52* (2013.01); *A61B 6/542* (2013.01); *A61B 6/582* (2013.01); *A61B 6/585* (2013.01); *H04N 5/32* (2013.01)

(58) Field of Classification Search
    CPC ......... A61B 6/426; A61B 6/4208; A61B 6/52; A61B 6/5205; A61B 6/542; A61B 6/582; A61B 6/585; H04N 5/32

USPC .................. 378/62, 98.8, 98.12, 208, 207; 250/370.09

See application file for complete search history.

(56) References Cited

U.S. PATENT DOCUMENTS

| | | | | |
|---|---|---|---|---|
| 5,668,375 | A | * 9/1997 | Petrick | H04N 5/325 250/208.1 |
| 5,818,898 | A | 10/1998 | Tsukamoto et al. | |
| 5,920,070 | A | * 7/1999 | Petrick | H04N 5/325 250/370.09 |
| 6,453,008 | B1 | * 9/2002 | Sakaguchi | H04N 5/32 250/370.09 |

(Continued)

FOREIGN PATENT DOCUMENTS

| | | |
|---|---|---|
| EP | 1 933 381 B1 | 5/2012 |
| JP | 2010-206819 | 9/2010 |
| JP | 2011-193306 | 9/2011 |

OTHER PUBLICATIONS

International Search Report dated Dec. 9, 2014 for International Application No. PCT/US2014/055975, 3 pages.

*Primary Examiner* — Allen C. Ho

(57) ABSTRACT

A radiographic detector acquires a first partial exposed image signal during an image readout of each of the rows of photosensors, one row at a time. A first scan of each row includes measuring the charge delivered to each cell of the rows, including some rows having partial charge and other rows having full charge, and obtaining a first null image signal during the scan. A second scan includes measuring remaining charge delivered to those rows having partial charge. The null image signal data is subtracted from a sum of the first two scans.

20 Claims, 9 Drawing Sheets

(56) References Cited

U.S. PATENT DOCUMENTS

| | | | | |
|---|---|---|---|---|
| 6,457,861 B1* | 10/2002 | Petrick | | A61B 6/032 |
| | | | | 378/207 |
| 6,707,881 B2* | 3/2004 | Boehm | | A61B 6/032 |
| | | | | 378/207 |
| 6,961,478 B2* | 11/2005 | Inoue | | G06T 5/20 |
| | | | | 358/450 |
| 7,399,974 B2* | 7/2008 | Spahn | | A61B 6/4441 |
| | | | | 250/370.09 |
| 7,532,706 B2* | 5/2009 | Kameshima | | A61B 6/00 |
| | | | | 250/214 AG |
| 7,645,995 B2* | 1/2010 | Yagi | | H04N 3/1568 |
| | | | | 250/370.09 |
| 7,810,997 B2* | 10/2010 | Okamura | | A61B 6/5235 |
| | | | | 378/207 |
| 7,832,928 B2* | 11/2010 | Topfer | | G06T 5/50 |
| | | | | 250/370.09 |
| 8,633,447 B2* | 1/2014 | Watanabe | | H04N 5/32 |
| | | | | 250/370.09 |
| 8,710,446 B2* | 4/2014 | Inoue | | G01T 1/2928 |
| | | | | 250/252.1 |
| 8,785,871 B2* | 7/2014 | Muraoka | | A61B 6/4233 |
| | | | | 250/370.09 |
| 8,809,796 B2* | 8/2014 | Jung | | G01T 1/247 |
| | | | | 250/370.08 |
| 8,953,744 B2* | 2/2015 | Watanabe | | H04N 5/32 |
| | | | | 250/370.09 |
| 8,983,036 B2* | 3/2015 | Tredwell | | G01T 1/2018 |
| | | | | 250/370.01 |
| 9,024,244 B2* | 5/2015 | Amitani | | H01L 27/14618 |
| | | | | 250/208.1 |
| 9,036,783 B2* | 5/2015 | Liu | | H04N 5/32 |
| | | | | 378/6 |
| 9,050,059 B2* | 6/2015 | Kuwabara | | A61B 6/542 |
| 9,055,238 B2* | 6/2015 | Oda | | H04N 5/3765 |
| 9,063,239 B2* | 6/2015 | Oda | | G01T 1/24 |
| 9,078,624 B2* | 7/2015 | Sugizaki | | G01T 1/2928 |
| 9,097,809 B2* | 8/2015 | Tredwell | | G01T 1/2018 |
| 9,195,899 B2* | 11/2015 | Topfer | | G06K 9/38 |
| 9,247,163 B2* | 1/2016 | Sato | | G01T 1/247 |
| 9,258,497 B2* | 2/2016 | Tsuji | | H04N 5/32 |
| 9,259,201 B2* | 2/2016 | Sato | | A61B 6/4233 |
| 9,288,409 B2* | 3/2016 | Iwashita | | H04N 5/32 |
| 9,369,639 B2* | 6/2016 | Kobayashi | | H04N 5/2178 |
| 9,395,450 B2* | 7/2016 | Tezuka | | H04N 5/2176 |
| 9,551,794 B2* | 1/2017 | Uchiyama | | G01T 1/17 |
| 9,554,759 B2* | 1/2017 | Hawver | | A61B 6/4225 |
| 9,615,811 B2* | 4/2017 | Yamanaka | | A61B 6/5205 |
| 9,651,690 B2* | 5/2017 | Tredwell | | G01T 1/247 |
| 9,668,331 B2* | 5/2017 | Takahashi | | H04N 5/32 |
| 9,730,658 B2* | 8/2017 | Tajima | | H04N 5/32 |
| 9,743,018 B2* | 8/2017 | Iwashita | | A61B 6/4233 |
| 9,753,158 B2* | 9/2017 | Nishino | | A61B 6/582 |
| 9,774,794 B2* | 9/2017 | Sakino | | H04N 5/32 |
| 9,780,128 B2* | 10/2017 | Tajima | | H05G 1/38 |
| 9,793,305 B2* | 10/2017 | Tajima | | G01T 1/2985 |
| 9,813,647 B2* | 11/2017 | Kobayashi | | G06T 5/40 |
| 9,820,703 B2* | 11/2017 | Wojcik | | A61B 6/4233 |
| 9,848,845 B2* | 12/2017 | Tajima | | H04N 5/32 |
| 9,880,111 B2* | 1/2018 | Oda | | H04N 5/32 |
| 9,892,521 B2* | 2/2018 | Enomoto | | A61B 6/4233 |
| 9,931,092 B2* | 4/2018 | Tajima | | A61B 6/488 |
| 9,959,602 B2* | 5/2018 | Kobayashi | | G06T 5/005 |
| 9,962,137 B2* | 5/2018 | Iijima | | A61B 6/4233 |
| 10,009,990 B2* | 6/2018 | Takenaka | | H04N 5/32 |
| 10,022,102 B2* | 7/2018 | Okada | | A61B 6/542 |
| 10,039,516 B2* | 8/2018 | Topfer | | A61B 6/4233 |
| 10,074,679 B2* | 9/2018 | Tajima | | A61B 6/4233 |
| 10,230,906 B2* | 3/2019 | Topfer | | H04N 5/32 |
| 2012/0138808 A1 | 6/2012 | Jung | | |
| 2013/0015327 A1 | 1/2013 | Amitani | | |

* cited by examiner

DIGITAL RADIOGRAPHY DETECTOR IMAGE READOUT PROCESS

CROSS REFERENCE TO RELATED APPLICATIONS

This application is a continuation of U.S. patent application Ser. No. 14/487,189, filed Sep. 16, 2014, issued as U.S. Pat. No. 9,554,759 B2 on Jan. 31, 2017, in the name of Hawver et al., entitled DIGITAL RADIOGRAPHY DETECTOR IMAGE READOUT PROCESS, which claims the benefit of U.S. Provisional Application U.S. Ser. No. 61/879,182, provisionally filed on Sep. 18, 2013, entitled "DR DETECTOR IMAGE READOUT PROCESS", in the names of Hawver, et al., which is hereby incorporated herein by reference in its entirety.

FIELD OF THE INVENTION

The invention relates generally to the field of medical imaging, and in particular to digital radiographic imaging and more particularly to apparatus and methods for enhancing the signal integrity of the image readout operation of a digital radiography detector.

BACKGROUND OF THE INVENTION

Stationary and mobile radiographic imaging equipment is employed in medical facilities to capture x-ray images on an x-ray detector. Such medical x-ray images may be captured using various techniques such as computed radiography (CR) and digital radiography (DR) in radiography detectors.

A related art DR imaging panel acquires image data from a scintillating medium using an array of individual sensors, arranged in a row-by-column matrix, in which each sensor provides a single pixel of image data. Each pixel generally includes a photosensor and a switching element that may be fabricated in a co-planar or a vertically integrated manner, as is generally known in the art. In these imaging devices, hydrogenated amorphous silicon (a-Si:H) is commonly used to form the photodiode and the thin-film transistor switch needed for each pixel. In one known imaging arrangement, a frontplane includes an array of photosensitive elements, and a backplane includes an array of thin-film transistor (TFT) switches.

However, there is a need for improvements in the consistency and quality of medical x-ray images, particularly when obtained by an x-ray apparatus designed to operate with a-Si DR detectors. There is also a need for detection of an x-ray exposure event without requiring that an x-ray exposure be delayed until the DR detector is ready, such as having external hardware connections that link to and hold off the x-ray source control electronics. Further, there is a need for detection of extraneous signals produced by nearby sources of low frequency magnetic fields before an x-ray exposure and an imaging readout operation is initiated.

BRIEF DESCRIPTION OF THE INVENTION

It would be advantageous to provide a method and apparatus to detect extraneous low frequency magnetic fields near image readout circuitry before an x-ray exposure and an imaging readout operation is performed. This capability provides the benefit of alerting the operator of a DR system to this noise condition and minimizes radiation exposure to a patient that produces DR images not meeting clinical diagnostic standards. It would also be advantageous to provide a method for the removal of image artifacts generated when the image readout process runs concurrently or overlaps with the x-ray beam exposure.

In one embodiment, an area x-ray detector is disclosed comprising a number of electrically-chargeable photosensitive cells arranged in rows and columns. Electric circuits, or charge integrators, are attached to the cells of each column by controllable row selecting switches to provide a reading of charge delivered to the cells of each column. Acquisition control electronic circuitry is programmed to acquire a first partial exposed image signal during a readout of each of the rows of cells one row at a time, a first scan of a current row including measuring the total charge delivered to each cell of the row using the electric circuits, resetting the electric circuits, restoring the charge of each cell of the current row by means of the electric circuits; acquiring a first null image signal during the readout of each of the rows of cells one row at a time, and acquiring a second scan of the current row including measuring the total charge delivered to each cell of the row by means of the electric circuits, and resetting the electric circuits.

In another embodiment, there is disclosed a method of operating an area x-ray detector that includes a plurality of electrically-chargeable photosensitive pixels arranged in rows and columns with charge integrator circuits attached to the pixels of each column to provide a reading of charge delivered to the pixels of each column. The method comprises acquiring a pair of signals during a dual scan of each of the rows of a portion of the pixels, one row at a time. The dual scan comprises a first scanning of each row including enabling the pixels of a current row for a first predetermined time period, measuring the total charge delivered to each pixel of the row by means of the charge integrator circuits, outputting the total charge to form a row of a first partial image signal, and a resetting of the charge integrator circuits and the pixels of the current row. A second scanning of each row includes disabling the pixels of the current row, measuring the charge delivered to each column of said each pixel of the current row by means of the charge integrator circuits, outputting the charge delivered to each column of said each cell to form a null image signal, and resetting the charge integrator circuits.

In another embodiment, a computer implemented method comprises scanning a charge level in a two dimensional array of pixels and recording in a first portion of electronic memory the charge level of the scanned pixels. The two dimensional array of pixels is exposed to radiographic radiation during the step of scanning which generates charges in the array of pixels such that scanning results in at least one of a first subset of the scanned pixels having a partial image charge. A second subset of the scanned pixels have a full image charge. The pixels are rescanned and recorded in a second portion of the electronic memory, and then the charge recorded in the first portion of the electronic memory and the charge recorded in the second portion of the electronic memory are summed. An advantage that may be realized in the practice of some disclosed embodiments of the DR imaging system and methods is improved readout of DR images by correcting artifacts caused by extraneous magnetic fields.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is further provided to introduce an illustrative selection of concepts in a simplified form that are described below in the detailed description, and is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention may be understood, a detailed description of the invention is disclosed with reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. For example, the summary descriptions above are not meant to describe individual separate embodiments whose elements are not interchangeable. In fact, many of the elements described as related to a particular embodiment may be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation. In the drawings, like numerals are used to indicate like parts throughout the various views. Thus, for further understanding of the invention, reference may be made to the following detailed description, read in connection with the drawings in which.

DETAILED DESCRIPTION OF THE INVENTION

Figure 1:
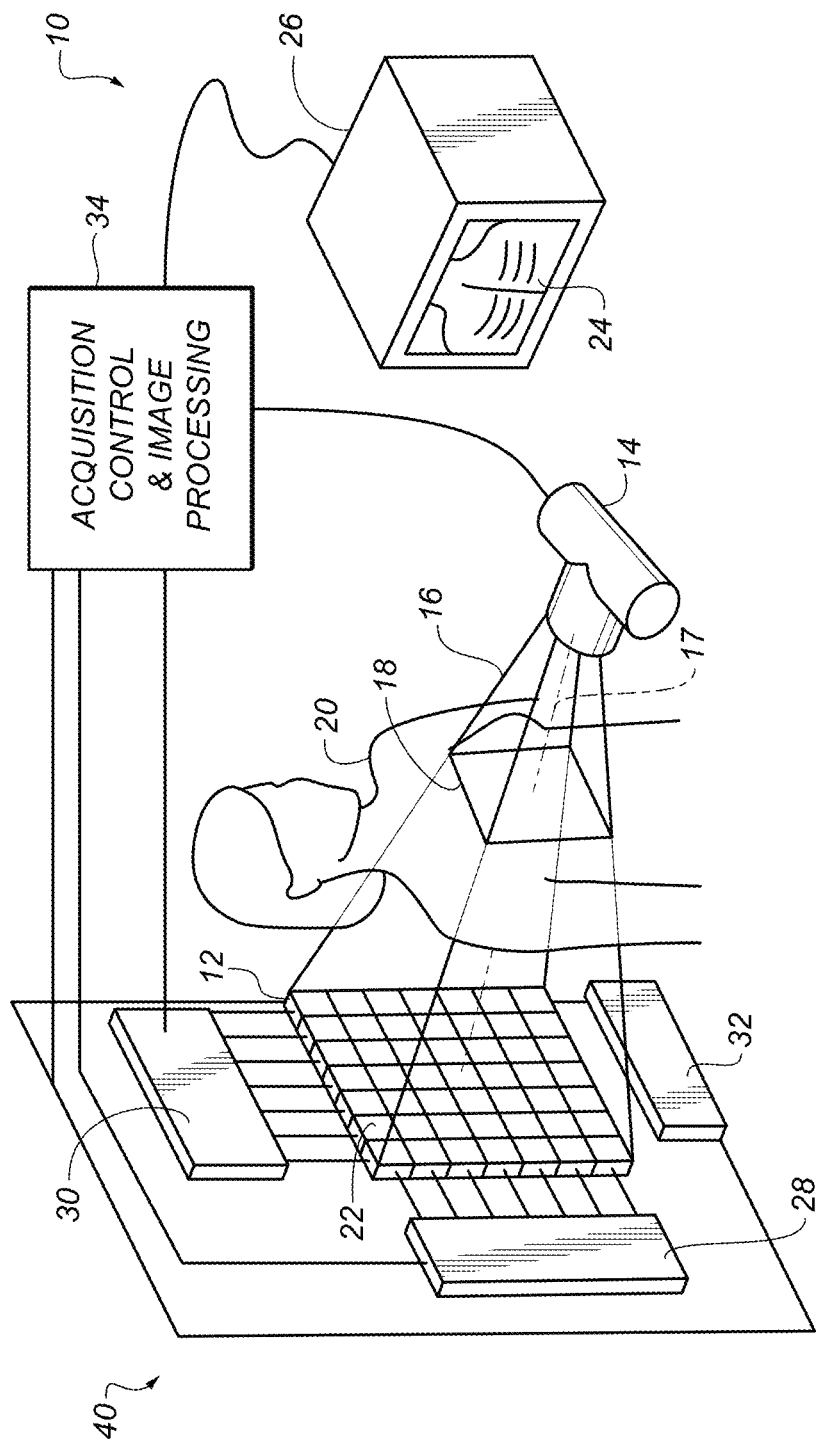
FIG. 1 is a perspective view of an exemplary radiographic imaging system.

During an imaging readout operation performed by a DR detector there may exist unwanted extraneous signals that affect the DR detector's readout operation by introducing data errors that result in degraded image quality when the image data is finally processed. The extraneous signals may originate from noise sources external to the detector or from sources within the detector housing. Extraneous signals may also be produced during the readout operation if the image readout occurs concurrently with an activation of the x-ray source. Extraneous magnetic fields may be generated by the DR system and related equipment in an imaging room which may cause parasitic effects in the readout circuitry or on the pixels in the photosensor array.

One type of external extraneous signal commonly found to interfere with DR detector image readout operations is caused by low frequency magnetic fields in the range of about one kilohertz up to hundreds of kilohertz. These magnetic fields may be produced by electrical equipment in close proximity to the DR detector. Typically, these noise inducing magnetic fields are generated by components such as inductors or AC motors that emit magnetic flux. Another source of extraneous noise includes power supplies that generate high voltages. These power supplies are often required by automatic exposure control hardware used with DR detectors.

Extraneous noise affecting operations of the DR detector find entry points into the DR detector via parasitic capacitance intrinsic to the pixel array of the DR detector. A DR detector's readout operation may be performed after an x-ray source has exposed the patient and detector to x-ray radiation for a fixed exposure period predetermined and configured by an operator. The corresponding DR detector integration period, which is concurrent with the x-ray source "on time", may be configured to terminate after the x-ray source is turned off, because the image readout process normally follows the DR detector integration period. A portion of an image readout process occurring during the x-ray source exposure period is susceptible to the noise signals caused by the x-ray source.

There may be occasions when it is desirable to perform the image readout concurrently with the x-ray exposure. In this case the image readout from the DR detector may be initiated before the x-ray source exposure process has begun. The image readout process may run continuously until all image frames are acquired and stored.

The start of an x-ray exposure may be detected by image processing software running concurrently with the readout process where the image processing software tests each read out image row for increased signal intensity. After the start of the x-ray beam exposure is detected, the row by row image readout continues until the signal level returns to a pre-exposure level at about zero. After the x-ray beam exposure period has finished, the image readout process continues for at least one more image readout cycle to obtain a final 'image free' frame (unexposed) of data called a dark image, or lag image, that is used to adjust and correct previous image data frames. When all collected image frames have been stored in an image buffer, which may include an image buffer internal to the DR detector comprising electronic memory locations for storing several image data frames, a post image processing function is performed on the buffered image frames to produce the final image. This method of image readout for a DR detector has the benefit of providing asynchronous image readout of an x-ray exposure event without the need for invasive external hardware connections linking to and holding off the x-ray source control electronics until the DR detector system is ready for an x-ray exposure. This image readout method, however, causes image artifacts induced in part by parasitic capacitance and x-ray beam exposure that generate leakage current during the readout method.

FIG. 1 is a perspective view of a digital radiographic (DR) imaging system 10 that includes a generally planar DR detector 40 (shown without a housing for clarity of description), an x-ray source 14 configured to generate radiographic energy (x-ray radiation), and a digital monitor 26 configured to display images captured by the planar DR detector 40, according to one embodiment. The planar DR detector 40 may include a two dimensional array 12 of photosensitive detector cells 22 (photosensors), arranged in electronically addressable rows and columns. The planar DR detector 40 may be positioned to receive x-rays 16 passing through a subject 20 during a radiographic energy exposure, or radiographic energy pulse, emitted by the x-ray source 14. As shown in FIG. 1, the digital radiography (DR) imaging system 10 may use an x-ray source 14 that emits collimated x-rays 16, e.g. an x-ray beam, selectively aimed at and passing through a preselected region 18 of the subject 20. The x-rays 16 may be attenuated by varying degrees along its plurality of rays according to the internal structure of the subject 20, which attenuated rays are detected by the two-dimensional array 12 of photosensitive detector cells 22. The planar DR detector 40 is positioned, as much as possible, in a perpendicular relation to a substantially central ray 17 of the plurality of x-rays 16 emitted by the x-ray source 14. The two-dimensional array 12 of individual photosensitive detector cells (pixels) 22 may be electronically read out (scanned) by their position according to column and row. As used herein, the terms "column" and "row" refer to the vertical and horizontal arrangement of the photosensitive detector cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject 20 of a DR imaging system 10, as the term is used herein, may be a human, an animal, an inanimate object, or a portion thereof.

In one exemplary embodiment, the rows of photosensitive detector cells 22 may be scanned one or more at a time by electronic scanning circuit 28 so that the exposure data from the two-dimensional array 12 may be transmitted to electronic read-out circuit 30. Each photosensitive detector cell 22 may independently store a charge proportional to an intensity, or energy level, of the attenuated radiographic radiation, or x-rays 16, received and absorbed in the photosensitive detector cell 22. Thus, each photosensitive detector cell 22, when read-out, provides information defining a pixel of a radiographic image 24, e.g. a brightness level or an amount of energy absorbed by the pixel, that may be digitally decoded by an acquisition control and image processing unit 34 and transmitted to be displayed by the digital monitor 26 for viewing by a user. An electronic bias circuit 32 is electrically connected to the two-dimensional array 12 to provide a bias voltage to each of the photosensitive detector cells 22.

Each of the electronic bias circuit 32, the electronic scanning circuit 28, and the electronic read-out circuit 30, may communicate with an acquisition control and image processing unit 34 over a connected cable (wired), or the planar DR detector 40 may be equipped with a wireless transmitter to transmit radiographic image data wirelessly to the acquisition control and image processing unit 34. The acquisition control and image processing unit 34 may include a processor and electronic memory (not shown) to control operations of the planar DR detector 40 as described herein, including control of circuits 28, 30, and 32, for example, by use of programmed instructions. The acquisition control and image processing unit 34 may also be used to control activation of the x-ray source 14 during a radiographic exposure, controlling an x-ray tube electric current magnitude, and thus the fluence of x-rays 16 in x-ray beam, and the x-ray tube voltage, and thus the energy level of the x-rays 16 in x-ray beam.

The acquisition control and image processing unit 34 may store a plurality of data frames received from the planar DR detector 40 and transmit image (pixel) data to the digital monitor 26, based on the radiographic exposure data received from the two-dimensional array 12 of photosensitive detector cells 22 in the planar DR detector 40. Alternatively, acquisition control and image processing unit 34 may process the image data and store it, or it may store raw unprocessed image data, in local or remotely accessible memory.

With regard to a direct detection embodiment of planar DR detector 40, the photosensitive detector cells 22 may each include an x-ray sensing element sensitive to x-rays 16, i.e. it absorbs x-rays 16 and generates an amount of charge carriers in proportion to a magnitude of the absorbed x-ray energy. A switching element may be configured to be selectively activated to read out the charge level of a corresponding x-ray sensing element. With regard to an indirect detection embodiment of a planar DR detector 40, photosensitive detector cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, is disposed over the light sensitive sensing elements to convert incident x-ray radiographic energy to visible light energy. Thus, in the embodiments disclosed herein, it should be noted that the planar DR detector 40 may include an indirect or direct type of planar DR detector 40.

Examples of sensing elements used in a two-dimensional array 12 include various types of photoelectric conversion devices (e.g., photosensors) such as photodiodes (P-N or PIN diodes), photo-capacitors (MIS), phototransistors or photoconductors. Examples of switching elements used for signal read-out include MOS transistors, bipolar transistors and other p-n junction components.

Figure 2:
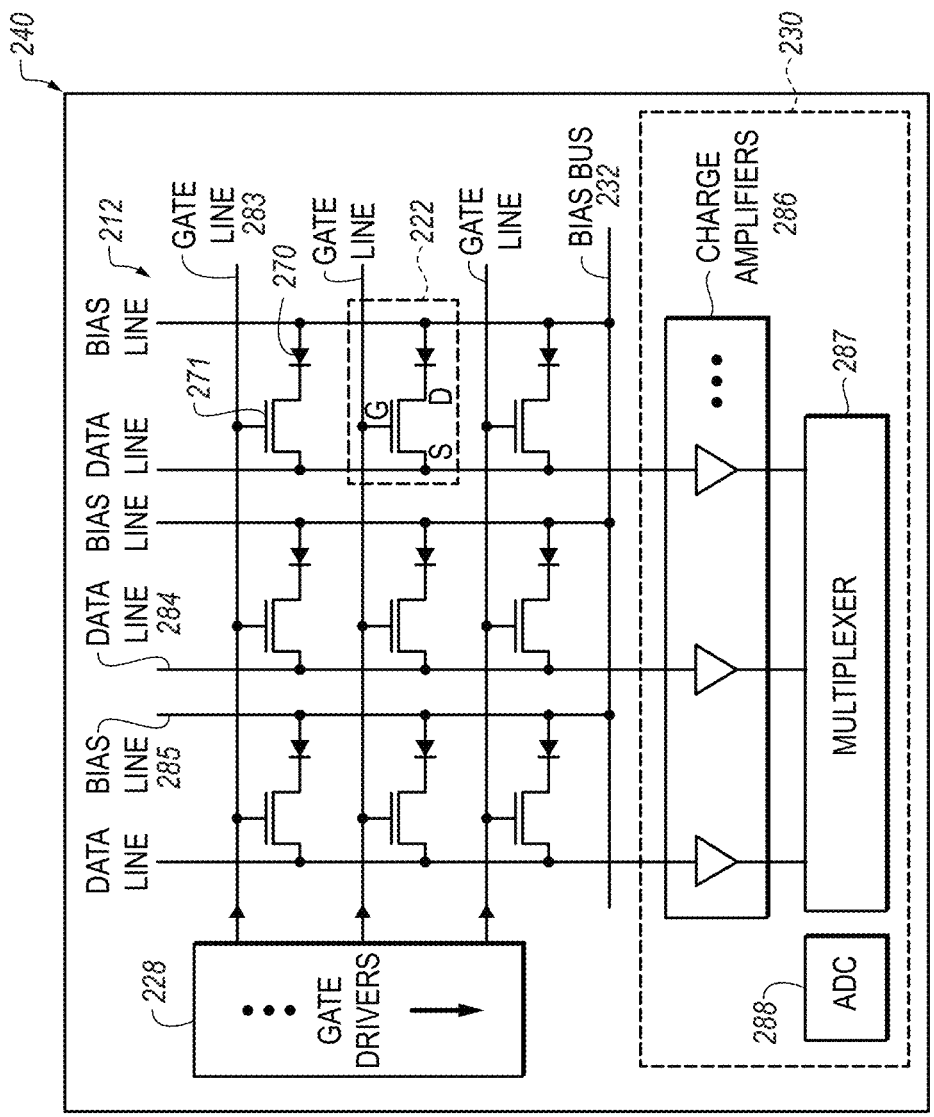
FIG. 2 is a schematic diagram of a portion of an exemplary imaging array for a DR detector used in the exemplary radiographic imaging system of FIG. 1.

FIG. 2 is a schematic diagram 240 of a portion of a two-dimensional array 12 for the planar DR detector 40. The array of photosensor cells 212, whose operation may be consistent with the two-dimensional array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of planar DR detector 40 disclosed herein, such as a multilayer DR detector, the two-dimensional array 12 may be formed in a device layer that abuts adjacent layers of the DR detector structure. A plurality of gate driver circuits 228 may be electrically connected to a plurality of gate lines 283 which control a voltage applied to the gates of TFTs 271, a plurality of readout circuits 230 may be electrically connected to a plurality of data lines 284, and a plurality of bias lines 285 may be electrically connected to a bias line bus or a variable bias reference voltage line 232 which controls a voltage applied to the photodiodes 270. Charge amplifier circuits 286 may be electrically connected to the data lines 284 to receive signals therefrom. Outputs from the charge amplifier circuits 286 may be electrically connected to a multiplexer 287, such as an analog multiplexer, then to an analog-to-digital converter (ADC) 288, or they may be directly connected to the ADC 288, to stream out the digital radiographic image data at desired rates. In one embodiment, the schematic diagram of FIG. 2 may represent a portion of a planar DR detector 40 such as an a-Si:H based indirect flat panel imager.

Incident x-rays 16, or x-ray photons, are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 may control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the p-n junction of each of the photodiodes 270 to enhance its collection efficiency for the charges generated by incident light rays. The image signal represented by the array of photosensor cells 212 may be integrated by the photodiodes 270 while their associated TFTs 271 are held in a non-conducting (off) state, for example, by maintaining the gate lines 283 at a negative voltage via the gate driver circuits 228. The array of photosensor cells 212 may be read out by sequentially switching rows of the TFTs 271 to a conducting (on) state by means of the gate driver circuits 228. When a row of the detector cells 222 is switched to a conducting state, for example by applying a positive voltage to the corresponding gate line 283, collected charge from the photodiodes 270 in those detector cells 222 may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifier circuits 286 to an analog-to-digital converter (ADC) 288 using a parallel-to-serial converter, such as multiplexer 287, which together comprise read-out circuit 230.

This digital image information may be subsequently processed by acquisition control & image processing unit 34 to yield a digital image which may then be digitally stored and immediately displayed on digital monitor 26, or it may be displayed at a later time by accessing the digital electronic memory containing the stored image. The flat panel DR detector 40 having an imaging array as described with reference to FIG. 2 is capable of both single-shot (e.g., static, radiographic) and continuous (e.g., fluoroscopic) image acquisition.

Figure 3:
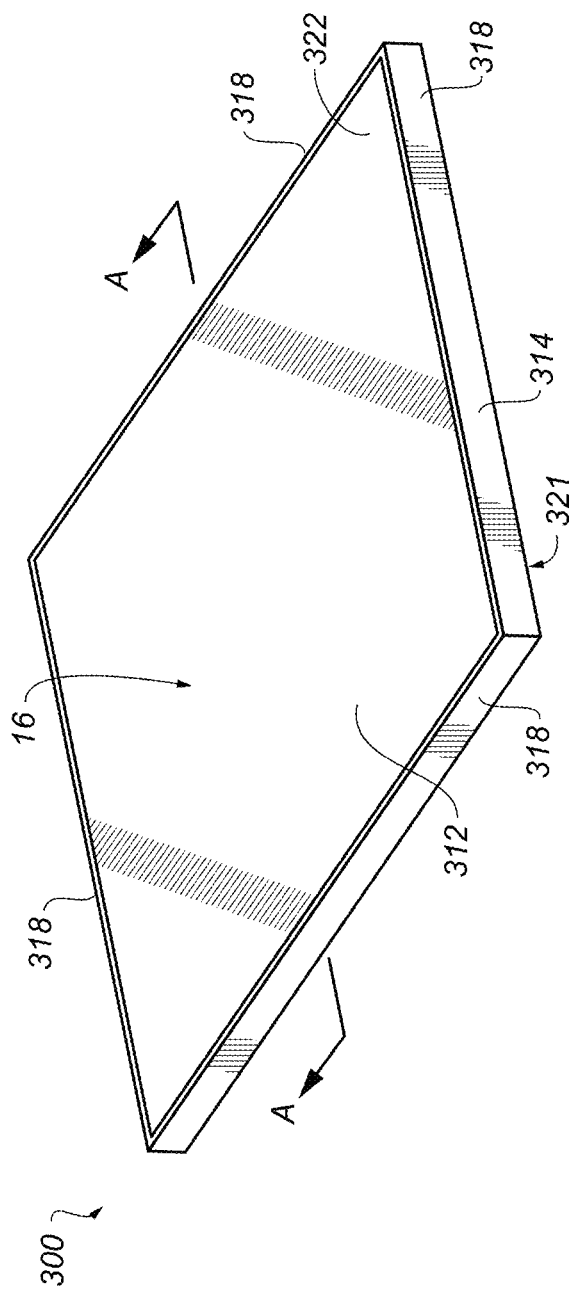
FIG. 3 shows a perspective view of an exemplary portable wireless DR detector.

FIG. 3 shows a perspective view of an exemplary prior art generally rectangular, planar, portable wireless DR detector 300 according to an embodiment of DR detector 40 disclosed herein. The DR detector 300 may include a housing 314 that encloses a multilayer structure comprising the photosensitive detector cells 22 of the DR detector 300. The housing 314 of the DR detector 300 may include a continuous, rigid, radio-opaque enclosure surrounding an interior volume of the DR detector 300. The housing 314 may comprise four orthogonal edges 318 and a bottom side 321 disposed opposite a top side 322 of the DR detector 300. A top cover 312 encloses the top side 322 which, together with the housing 314 substantially encloses the multilayer structure in the interior volume of the DR detector 300, and may be attached to the housing 314 to form a seal therebetween. The top cover 312 may be made of a material that passes x-rays 16 without significant attenuation thereof, i.e., a radiolucent material, such as a carbon fiber or plastic material.

Figure 4:
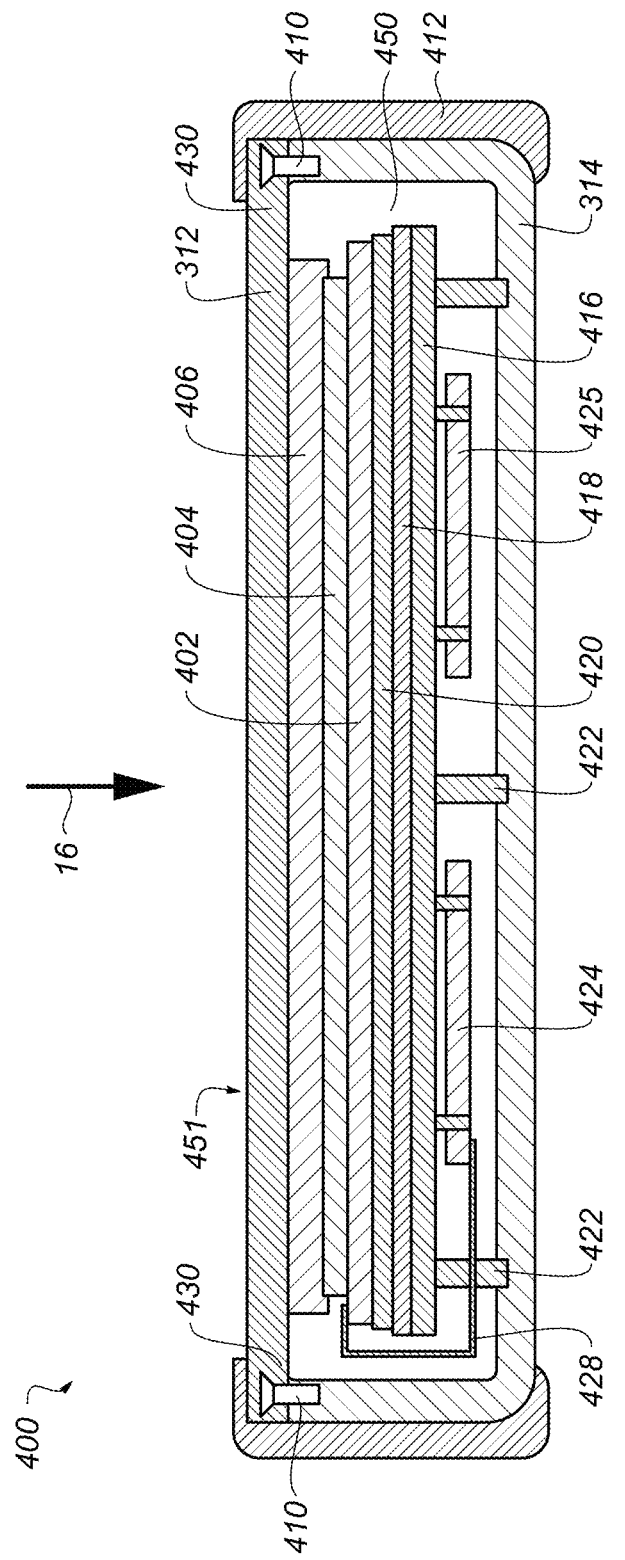
FIG. 4 is an exemplary cross-sectional view along section line A-A of the portable wireless DR detector of FIG. 3.

With reference to FIG. 4, there is illustrated in schematic form an exemplary cross-section view along section A-A of the exemplary embodiment of the DR detector 300 (FIG. 3). For spatial reference purposes, one major surface of the DR detector 400 may be referred to as the top side 451 and a second major surface may be referred to as the bottom side 452, as used herein. The multilayer imaging structure is disposed within the interior volume 450 enclosed by the housing 314 and top cover 312 and may include a scintillator layer 404 over the two-dimensional array 12 shown schematically as the device layer 402. The scintillator layer 404 may be directly under (e.g., directly connected to) the radiolucent top cover 312, and the device layer 402 may be directly under the scintillator layer 404. Alternatively, a flexible layer 406 may be positioned between the scintillator layer 404 and the top cover 312 as part of the multilayer structure to provide shock absorption. The flexible layer 406 may be selected to provide an amount of flexible support for both the top cover 312 and the scintillator layer 404, and may comprise a foam rubber type of material.

A substrate layer 420 may be disposed under the device layer 402, such as a rigid glass layer upon which the device layer 402 is formed, and may comprise another layer of the multilayer structure. Under the substrate layer 420 a radio-opaque shield layer 418 may be used as an x-ray blocking layer to help prevent scattering of x-rays 16 passing through the substrate layer 420 as well as to block x-rays 16 reflected from other surfaces in the interior volume 450. Readout electronics, including the electronic scanning circuit 28, the electronic read-out circuit 30, and the electronic bias circuit 32 (FIG. 1) may be formed co-planar with the device layer 402 or, as shown, may be disposed below frame support member 416 in the form of integrated circuits electrically connected to printed circuit boards 424, 425. The frame support member 416 is fixed to the housing 314 using frame support beams 422 to provide support for the multilayer structure just described. The device layer 402 is electrically connected to the readout electronics, 28, 30, 32, over a flexible connector 428 which may comprise a plurality of flexible, sealed conductors. X-rays 16 flux may pass through the radiolucent top panel cover 312, in the direction represented by exemplary x-rays 16, and impinge upon scintillator layer 404 where stimulation by the high-energy x-rays 16, or photons, causes the scintillator layer 404 to emit lower energy photons as visible light rays which are then received in the detector cells 222 of device layer 402. The frame support member 416 may securely mount the multilayer structure to the housing 314 and may further operate as a shock absorber by disposing elastic pads (not shown) between the frame support beams 422 and the housing 314. Fasteners 410, such as screws, may be used to fixedly attach the top cover 312 to the housing 314 and create a seal therebetween in the region 430 where they come into contact. In one embodiment, an external bumper 412 may be attached along the orthogonal edges 318 of the DR detector 400 to provide additional shock-absorption.

Figure 5:
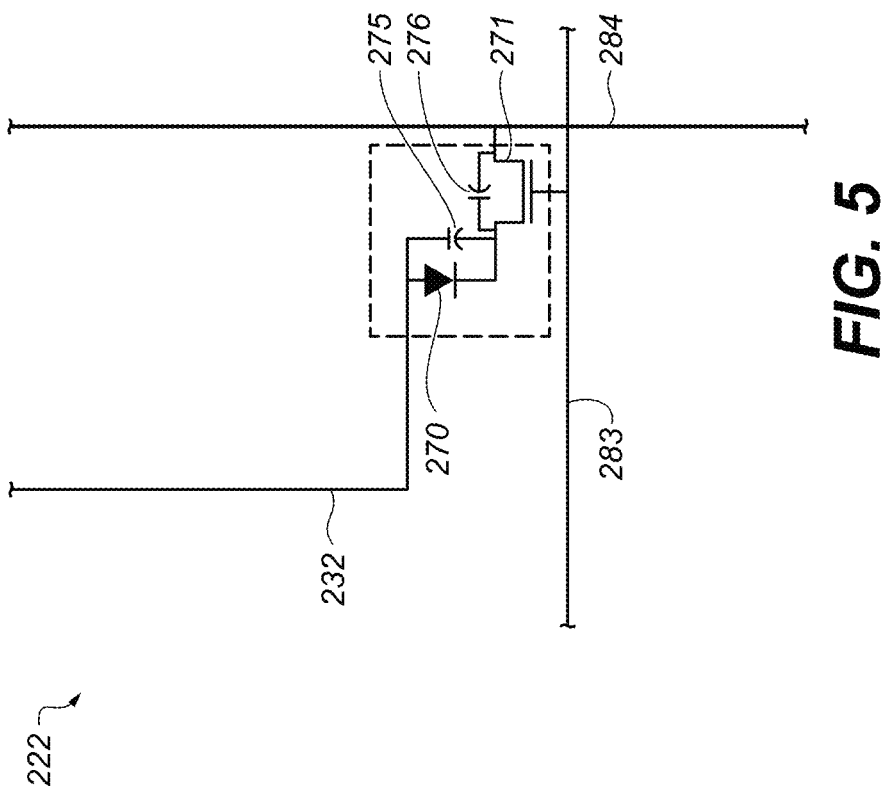
FIG. 5 is a diagram showing an exemplary pixel cell and selected constituent components.

FIG. 5 illustrates detector cell 222 connected to bias line bus 232, gate line 283, and data line 284, including a representation of a parasitic capacitance 276 between the source and drain of TFT 271. The parasitic capacitance 276 couples the cathode of photodiode 270 to data line 284. The parasitic capacitance 276 introduces a noise signal into the data line 284 during an image readout operation by creating a low impedance path around TFT 271 even when the TFT 271 is in a high impedance 'OFF' state. The charge storage capability of the photodiode 270 is represented by the capacitance 275.

Figure 6B:
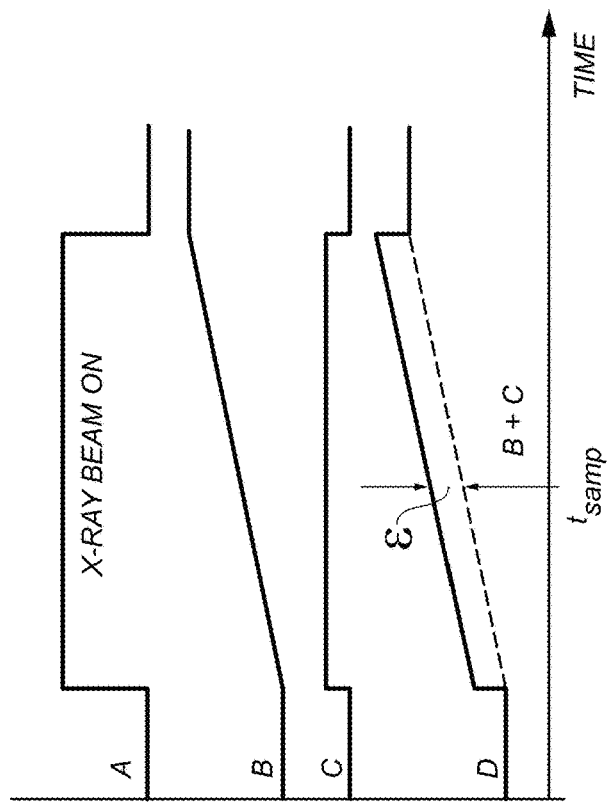
FIGS. 6A-B illustrate an exemplary pixel cell showing the generation of extraneous signals.
Figure 6A:
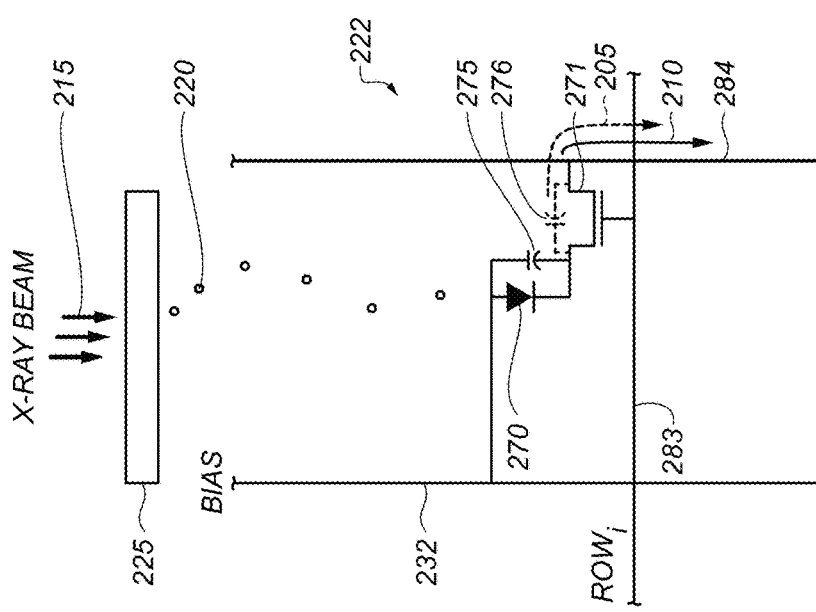

FIG. 6A illustrate an exemplary deleterious process occurring in the detector cell 222 caused by effects of the extraneous signals. FIG. 6A includes two representative signal paths from photodiode 270. First signal path 210 is connected from the cathode of photodiode 270 through TFT 271 and out to data line 284 toward downstream read out circuitry, and is designed to carry DR detector image signals. The second signal path 205 is a parasitic signal path that bypasses TFT 271 via a parasitic capacitance 276 which effectively couples the drain and source of the TFT 271. This first signal path 210 is created when TFT 271 is switched to the low impedance 'ON' state using a signal on the gate line 283 delivered by a gate driver connected to the gate line 283. This first signal path 210 is the designed signal conduction path and is used during an image readout operation to read out the charge level stored in the photodiode 270 via its capacitive property, represented by capacitance 275. The parasitic capacitance 276 may be referred to as a leakage capacitance that creates a low impedance conductive path for time varying (non-DC) signals. An x-ray exposure period causes such a time varying signal due to the integration time wherein charge accumulates in the photodiode 270 via a photon generated photodiode current, and so causes leakage into the data line 284 across the parasitic capacitance 276. An exemplary x-ray beam (photons) 215 may be received at the detector cell 222, initially impacting a scintillator layer 225 which, in response to the x-ray photons, emits light photons 220. Light photons 220, in turn, impact photodiode 270 which, in response, generates charge carriers which are accumulated in the photodiode 270 due to its intrinsic capacitance 275.

The graph of FIG. 6B illustrates a plot of various waveforms on its vertical axis versus time, on its horizontal axis. Waveform A represents an x-ray pulse of finite duration received by the detector cell 222. While the x-ray pulse impacts the detector cell 222, charge carriers accumulate in the photodiode 270 which is represented as a voltage ramp-up in waveform B. The voltage ramp B may be represented as a time-varying voltage (dv/dt) and so causes a leakage across the parasitic capacitance 276, represented by the leakage current waveform C, through the second signal path 205 as described above. Thus, the total signal as measured on data line 284, represented by total signal waveform D, during an x-ray pulse includes the sum of the pixel voltage (waveform B) plus the erroneous and extraneous leakage current of waveform C. As shown in the total signal waveform D at time $t_{samp}$, an error ε is caused by the leakage current. The time varying voltage produces leakage current over the second signal path 205 even when TFT 271 is in the high impedance 'OFF' state. This leakage current is the source of the extraneous data line signal caused by an x-ray exposure performed concurrently with an image readout operation.

During image readout of any pixel, an extraneous leakage current signal will be present on the data line and will equal the summed total of all other leakage currents in the pixels connected to the same data line, i.e. a column of pixels, by their parasitic capacitance 276. This results in an image readout error that is present only during the time that the pixel photosensor array receives x-ray fluence during an x-ray exposure. Image readout and x-ray exposure duration will rarely be equivalent, therefore, to insure that the image readout operation acquires all image data (photosensor charge), the image readout operation may be configured to extend longer in time than the x-ray exposure. This configuration will result in a part, but not all, of the image readout time duration to be affected by the extraneous leakage current.

Figure 7:
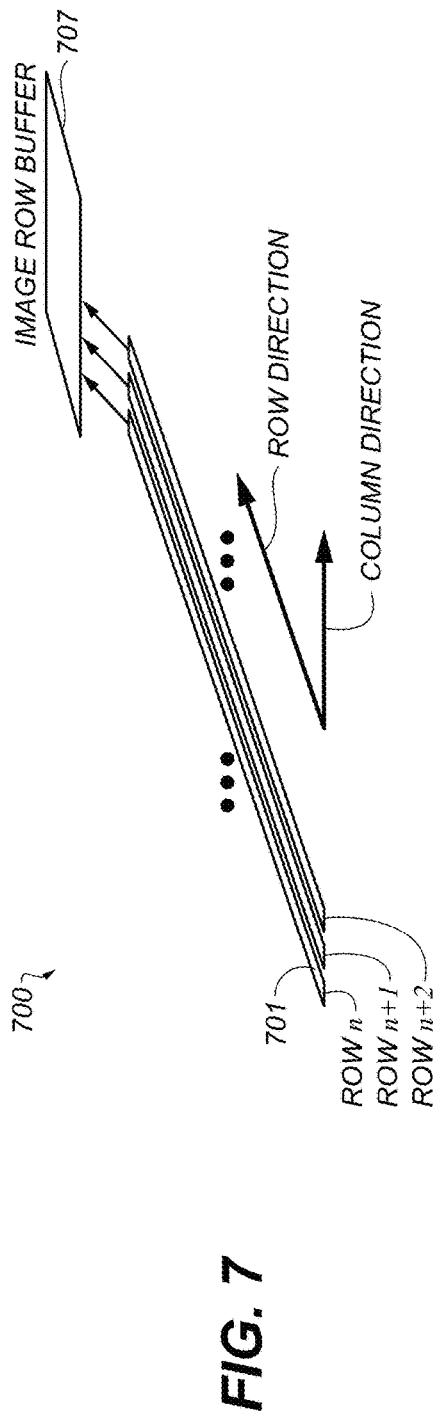
FIG. 7 is a diagram showing an exemplary readout process for an image readout operation in a DR detector.
Figure 8:
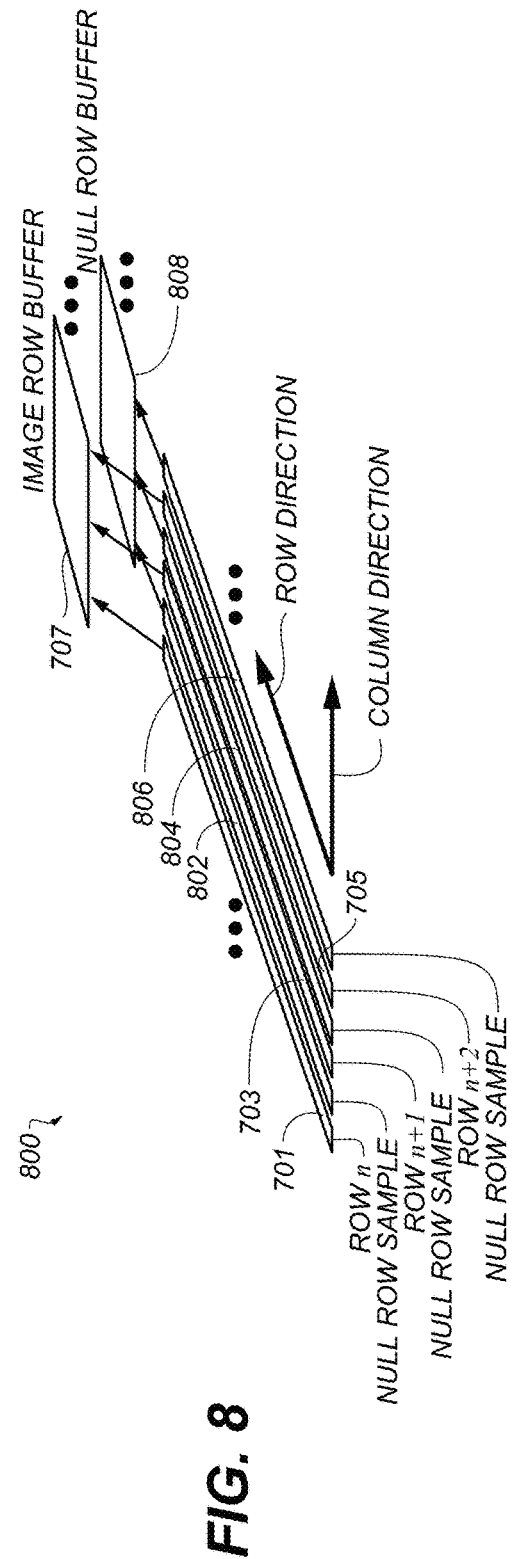
FIG. 8 is a diagram showing an exemplary image readout process using an interleaved null row read process for a DR detector.

FIG. 7 illustrates one embodiment of an image readout process 700 wherein rows of pixels n 701, n+1 703, n+2 705, and so on, are each read out one at a time in sequence and stored into the image row buffer 707. FIG. 8 illustrates an embodiment of a modified image readout process 800 using null row readouts 802, 804, 806, in a readout process to acquire complementary data sets that include image data information from image readouts 701, 703, 705 stored in image buffer 707, and extraneous signal data information from null row readouts 802, 804, 806, stored in null row buffer 808. The buffers 707, 808, may include electronic memory for storing a plurality of image data frames in different addressable portions of the electronic memory. Referring to FIG. 7 and FIG. 8, one modified image readout process embodiment may include successive image row 701, 703, 705, readouts that are interleaved with null row 802, 804, 806, readouts. Starting with read out of a particular image row n 701, the image data is digitized by A/D converters 288 (FIG. 2) and stored into the image row buffer 707 at a memory location corresponding to image row n 701. This image row readout is immediately followed by a null row 802 readout wherein the gate line 283 (FIG. 2) for that particular row of TFTs are turned off and any extraneous signal induced onto their corresponding data lines is digitized by A/D converters 288 and then stored into a null row buffer 808 at a memory location corresponding to image row n 701 of the image data. This interleaved process of alternate image row 701, 703, 705, readouts each followed by a null row 802, 804, 806, readout, respectively, may be termed a null row read operation and may be used to detect and capture extraneous signals present on the data lines 284.

A null row read operation is similar to the standard image row readout process except that during the null row read operation none of TFTs 271 of data lines 284 are set to the 'ON' state. For example, the null row read state may be achieved by keeping all row gate drivers 228 turned off while repeating the standard image row readout process. When a null row read process is performed the signal information acquired does not contain image information from the pixels' photodiodes 270 but rather may contain extraneous leakage signal information present on individual data lines 284.

Figure 9:
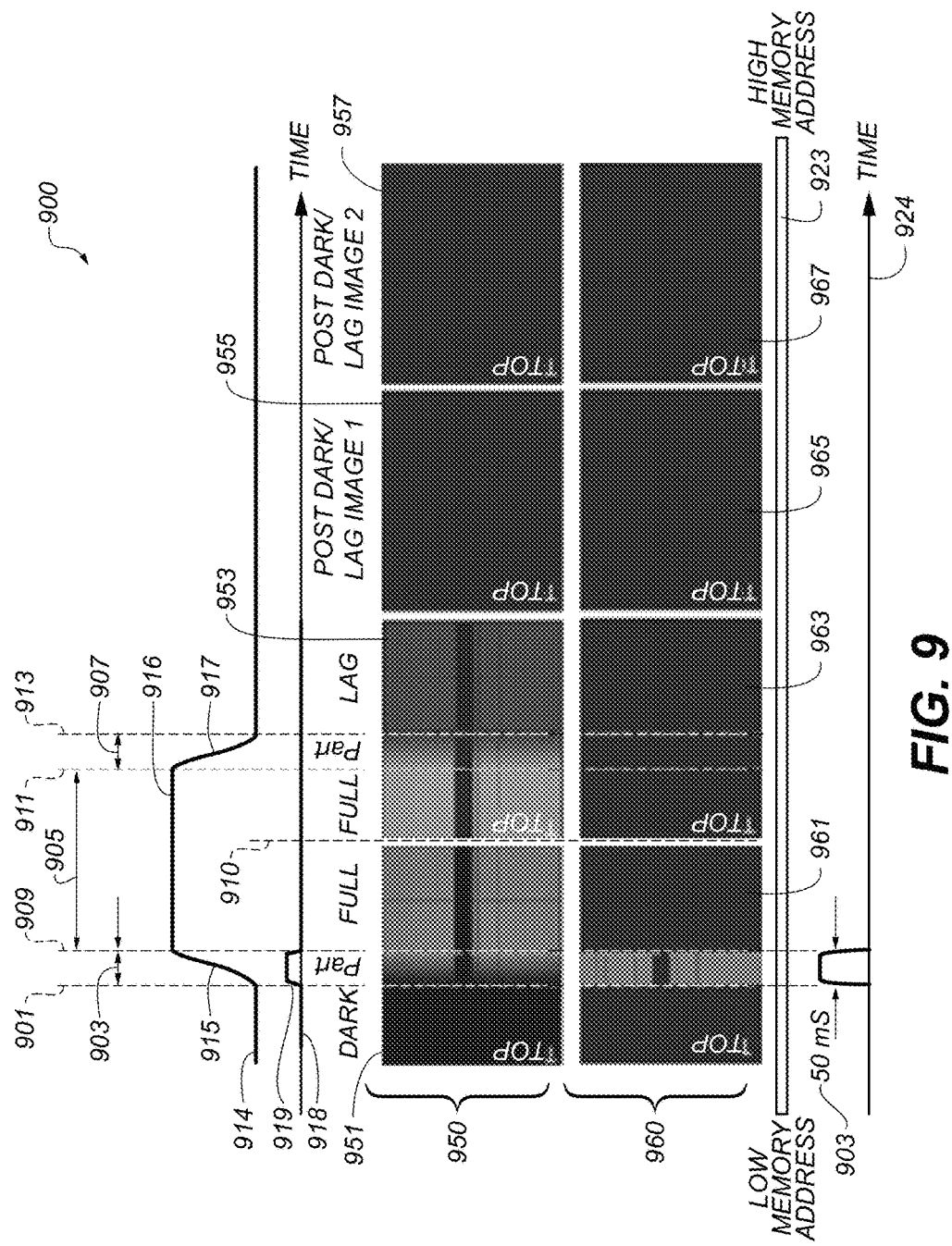
FIG. 9 is a diagram showing exemplary waveforms and image sets produced by an exemplary image readout procedure.

FIG. 9 illustrates a process 900 implementing complementary sets of image data frames 950, which set may include image data frames 951, 953, 955, and 957, and null row data frames 960, which set may include null row data frames 961, 963, 965, and 967. Each set, 950, 960, of data frames may include dark (or lag) image frames 955, 957, and dark (or lag) null row frames 965, 967, all data frames being acquired by performing the interleaved readout procedure as described herein with respect to FIG. 8. All the illustrated data frames 950, 960, may be stored in a storage buffer 923 comprising both the image row buffer 707 and null row buffer 808. With respect to a horizontal axis representing a time duration 924, the storage buffer 923 may include additional data frames captured during a time interval preceding a capture of the image and null row data frames 951, 961, respectively, and after a capture of the image and null row data frames, 957, 967, respectively. Thus, a null row data frame captured in a preceding time interval may include a band of extraneous signals such as illustrated in the null row data frame 961, which may be used to infer that extraneous magnetic flux is affecting operation of the DR detector. Such detection may be used to trigger a notification signal to the operator of the DR equipment to investigate potential sources of magnetic flux near the DR detector and to move such sources further from the DR equipment. As used herein, the term "frame" or "data frame" represents the data captured by the array of photosensor cells 212 in a DR detector 40. Rows of pixel data are oriented vertically in the perspective of FIG. 9, wherein the first row of pixel data is located to the left of each data frame, 951-957 and 961-967, labeled "TOP", and the last row of pixel data (i.e. bottom) is located at the rightmost end of each data frame, 951-957 and 961-967, in the perspective of FIG. 9. The rows of pixels in the DR detector are repeatedly read out from top to bottom to generate the data frames 951-957 and 961-967 as shown.

An x-ray source activation is illustrated as an exemplary 50 ms exposure 903 beginning at first point in time 901 and continuing until the x-ray source is deactivated, or turned off, at a second point in time 909. The amount of image data available to be read out from the array of photosensor cells 212 is represented by the graph 914. Points on the graph 914 correspond to rows of pixels being read out from a DR detector 40 providing the image data frames 950-960. The graph 914 indicates that, during the 50 ms exposure 903, an amount of image data available in x-ray exposed pixels increases from about a zero percentage level at the activation time point 901 to about a full 100% level 916 at the deactivation time point 909, as indicated by the rising portion 915 of the graph 914. Because a number of rows of image data are being read out during the rise time 915, each such row will have been read out without complete image data. Those rows being read out closer in time to the x-ray source activation point 901 will contain a smaller percentage of the full image data than the rows being read out closer in time to the x-ray source deactivation time point 909. Those rows being read out during the time duration 905, after the x-ray source deactivation time point 909, will contain a full 100% of the image data as indicated by the horizontal portion 916 of the graph 914. Note that during this full readout period 905 the last row of the DR detector's pixel array will have been read out, at about the time 910, to complete the data frames 951, 961, and that the DR detector readout will repeat, after about the time 910, starting at the DR detector's first row (TOP) to generate the next data frames 953, 963 (and repeating the readout for successive dark frames 955-957 and 965-967 as illustrated).

The falling portion 917 of the graph 914 represents an amount of data in corresponding rows of pixels that have not yet been read out. This may be understood by noting that the row of pixels being read out from the DR detector 40 corresponding to the point in time at about 901 is the same row of pixels being read out from the DR detector at the point in time at about 911 and the row of pixels being read out from the DR detector corresponding to the point in time at about 909 is the same row of pixels being read out from the DR detector at the point in time at about 913. Thus, the rows of pixels that were read out during the time period 903 contained partial image frame data (i.e., less than 100% due to the active x-ray exposure not having been completed) wherein the remaining unread portion of image frame data from those rows of pixels is read out during the time period 907. It may be noted that adding together the read out data from the rising and falling data portions 915, 917, respectively, results in a full 100% read out of available image data with respect to that portion (or rows) of the image data frame.

Activation of the x-ray source during the time period 903 causes an increase in charge carriers in each exposed detector cell 222 of the array of photosensor cells 212, which results in an induced time varying voltage in each exposed detector cell 222. As described herein, the time varying voltage (dv/dt) generates a parasitic signal 919, in the graph 918, in the pixels of the imaging array even when the readout TFTs 271 are not turned on. This parasitic effect is shown in the null row data buffer image 961 wherein extraneous signals are generated during the rising portion 915 of the graph 914 corresponding to the x-ray source activation time 901.

A complete DR image may be obtained from the DR detector data frames obtained thus far by first adding together the image data frames 951 and 953 which results in a 100% full read of the image frame data corresponding to an x-ray exposure 903, and then subtracting from that total the null row image data represented in the null row data frame 961. This combined image frame data may be comparable to the representation of the total data representing an x-ray exposure as described with reference to graph D of FIG. 6B, and the null row data frame may be comparable to the error data ε as shown in FIG. 6B. Subtraction of the error data (null row data frame 961) results in a more accurate DR image.

Figure 11:
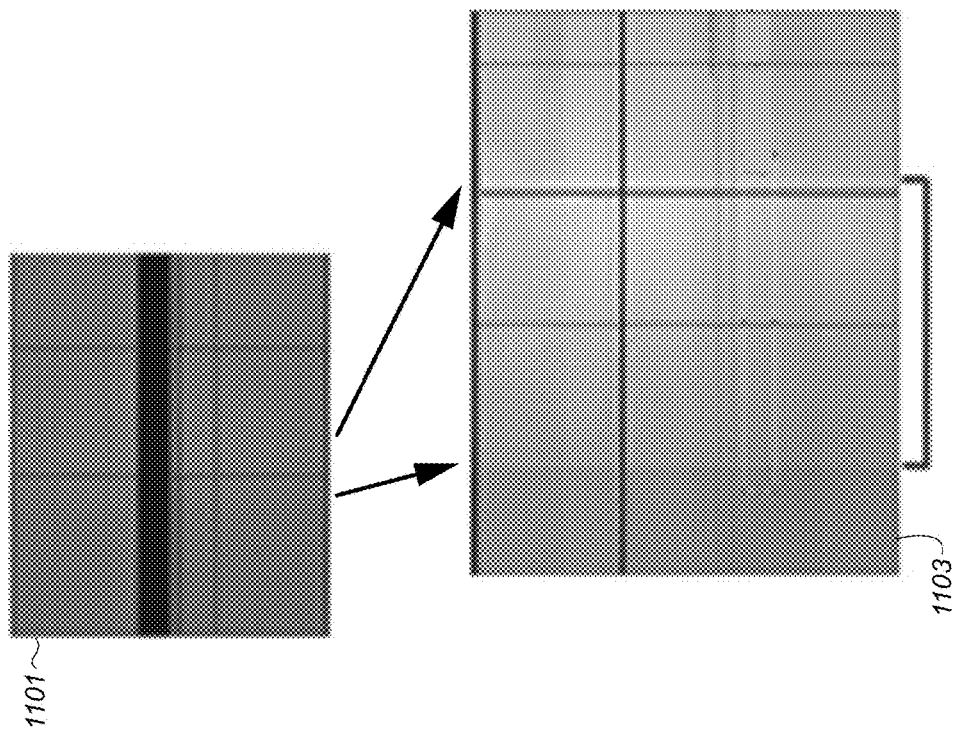
FIGS. 10-11 illustrate an exemplary reconstruction using two image data sets.
Figure 10:
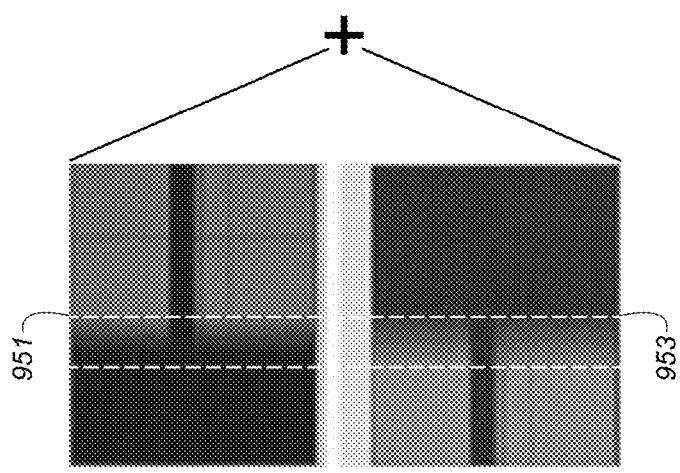

Referring now to FIGS. 10-11 there is illustrated an exemplary process of adding two image frames together as just described. Image data frame 951 is added to image data frame 953 to obtain a total image data frame 1101 for the x-ray exposure 903 which reconstructs all the image data collected and stored in the image buffer. The various image frames 951, 953, 961, may be stored in separate portions of the image buffer 923, and may be combined by addition or subtraction to replace in the buffer memory one of the combined images or, alternatively, the combined image may be stored in another portion of the image buffer. The extraneous noise artifact may not be visible in the combined image of 1101 but can be better observed in the magnified image wherein the parasitic signal can be seen in the segment 1103 of the magnified combined image. This is the portion of the total image data that is corrected via subtraction of the null row read data.

As exemplified herein, the image readout process for a DR detector system may be performed after an x-ray expose-integration period has occurred. The purpose of the image readout operation is to acquire x-ray exposed patient image data from the DR detector's pixel array produced by the expose-integration process. The image information may be sequentially read out from each pixel row of the detector array into an internal image buffer, as described herein. The first exposed image readout may be immediately followed by a second non-exposed-integration period, which may be performed during an interval when there is no incident x-ray radiation impinging the sensor array of the DR detector. Since no x-ray radiation is present during the non-exposed-integration period, there is no new image information in the second read out image (e.g., lag image 955). However, because the first image readout operation leaves a small percentage of signal data remaining in the detector pixel array, the second readout operation recovers this left over signal data. The second read out image is typically referred to as image lag or simply a dark image. These steps may be repeated to obtain a third non-exposed-integration operation image without x-ray radiation to obtain a second dark image frame. A post processing operation may be performed on the set of acquired image frames, e.g., the exposed image having one or two frames, the first non-exposed dark image frame and the second non-exposed dark image frame may be added together or otherwise processed, to produce the final artifact free DR detector image.

The complementary set of image data and null row data may then be processed to determine the magnitude of any extraneous signal present on the data lines during the image readout operation, as described herein. In one embodiment, when extraneous signal magnitude is above a certain threshold, it may be compensated or removed from the image data by a process of combining (e.g., subtracting, weighting) the null row data from the image readout data. Subtracting the null row data from the image readout data may reduce or remove extraneous signal noise from the image readout data because Null Row data does not contain image data information from the pixel sensor array.

One caveat to such methods is that because the image readout operation is not perfectly simultaneous with the null row read operation, there may be some error in any measured extraneous signal if the frequency components of the extraneous signal are a prescribed amount greater than (e.g., twice) the readout sampling frequency of the null row read operation. This condition violates the Nyquist sampling criterion and may produce an erroneous aliased signal in the null row read data. If these aliased signals are present then it may be difficult to remove the extraneous signals from the image data by subtracting the two image sets.

When it is likely that extraneous signal frequencies are higher than the readout sampling frequency an alternate method may be used. This method implements a series of null row read operations that are performed before an x-ray exposure process has been initiated and may be used to detect if there is extraneous signal noise from external low frequency magnetic fields present on the data lines before the x-ray exposure and image readout operation has started. In this case, successive null now reads are performed and the digitized data line signals are stored into a temporary row buffer similar to the buffers shown in FIG. 8. A real time digital processing algorithm is then applied to the data from the null row read operation to determine if any extraneous signal is present by comparing a magnitude, or intensity, of the data obtained to a threshold. While the frequencies of external magnetic fields will most likely be greater than the null row read sampling frequency the aliased signals in the null row read data is not a concern because this method only needs to detect that an extraneous signal was present.

According to exemplary embodiments, null row read data may be used in several ways to detect, compensate for, reduce and prevent extraneous signals from interfering with the standard image readout operation. One null row read process embodiment may be used to detect the presence of extraneous signals (e.g., null row read data) before an x-ray exposure occurs. As discussed previously, when the image readout operation is performed concurrently with an x-ray radiation exposure operation an extraneous signal is impressed on all data lines in the pixel array sensor. The magnitude of the extraneous signal on the individual data line is dependent on the number of photons at each of the photodiode sites along the entire data line and this is dependent on the intensity of x-ray fluence impinging the scintillator at the photodiode sites along the length of the data line.

Exemplary digital processing algorithms to detect extraneous noise on the data lines may be implemented in firmware and software using high speed digital processing electronics, such as Field Programmable Gate Arrays (FPGAs) and CPUs, which are placed internal to the DR detector system. If any extraneous signal is detected, this condition may be communicated by the DR detector system hardware and software to the operator through a visible/audible alert at the system console. The operator may then take preventative steps to remove the source of magnetic fields to avoid interference with the DR detector system image readout operation. This is especially useful for portable wireless DR detector systems which, when used by mobile x-ray units, may be operated in many different locations within a hospital or clinic.

When the image readout operation is complemented with an interleaved null row read operation according to embodiments described herein, means may be provided to perform the image readout operation during the x-ray exposure period and address or remove the inherent leakage current image artifact produced by parasitic capacitances in the pixel array sensor.

In one exemplary embodiment, an error produced by extraneous leakage current on the data line may be determined independent and separate from the image data by following an image row readout process with a corresponding null row read process. Since the leakage current is present on the data lines even when the TFTs are all turned off this provides a way to measure the extraneous leakage current right after at each image row read. Since the leakage current is measured separately and independently, it may be subtracted from the image data in a post process operation. Further, because the extraneous leakage current onto the data lines effectively remains at a constant level during the x-ray exposure, there is no danger that aliasing error will be present in the null row read data.

Using the methods described herein makes possible the detection of interference caused by low frequency magnetic fields that would degrade final image quality and thereby detecting and prevent such occurrence by alerting the operator of a DR detector system. Additionally, exemplary methods and system embodiments described herein may provide a capability to perform image readout operations during the x-ray expose operations and to be able to measure/monitor induced extraneous signals and compensate for or remove induced extraneous signals from the image data set to obtain final output images that are of clinical diagnostic quality.

As will be appreciated by one skilled in the art, the present invention may be embodied as a system, method, or computer program product. Accordingly, an embodiment of the present invention may be in the form of an entirely hardware embodiment, an entirely software embodiment (including firmware, resident software, micro-code, and other suitable encodings) or an embodiment combining software and hardware aspects that may all generally be referred to herein as a "circuit" or "system." Furthermore, the present invention may take the form of a computer program product embodied in a computer-readable storage medium, with instructions executed by one or more computers or host processors. This medium may comprise, for example: magnetic storage media such as a magnetic disk (such as a hard drive or a floppy disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that is connected to a host processor by way of the internet or other communication medium.

While the invention has been illustrated with respect to one or more implementations, alterations and modifications may be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. The term "at least one of" is used to mean one or more of the listed items may be selected. The term "about" indicates that the value listed may be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An x-ray detector comprising:
   a plurality of electrically-chargeable photosensitive cells arranged in rows and columns;
   electric circuits connected to the plurality of electrically-chargeable photosensitive cells of each column and row to perform one or more readouts of charge contained in the plurality of electrically-chargeable photosensitive cells;
   an acquisition control and image processing circuit programmed to:
      acquire one or more partial exposed image frames during the one or more readouts of charge contained in the plurality of electrically-chargeable photosensitive cells;
      acquire one or more dark frames during the one or more readouts of charge contained in the plurality of electrically-chargeable photosensitive cells after acquiring the one or more partial exposed image frames; and
      combine the one or more partial exposed image frames and the one or more dark frames acquired after the one or more partial exposed image frames.

2. The x-ray detector of claim 1, wherein the acquisition control and image processing circuit is further programmed to detect an x-ray exposure by testing each row of the plurality of electrically-chargeable photosensitive cells for increased image signal intensity.

3. The x-ray detector of claim 1, further comprising a buffer configured to store the one or more partial exposed image frames and the one or more dark frames.

4. The x-ray detector of claim 3, wherein the buffer is configured to store an x-ray image comprising the combined one or more partial exposed image frames and the one or more dark frames.

5. The x-ray detector of claim 1, wherein the acquisition control and image processing circuit is further programmed to acquire one or more null image frames during the one or more readouts of charge contained in the plurality of electrically-chargeable photosensitive cells.

6. The x-ray detector of claim 5, further comprising a buffer for storing image frames, wherein the buffer is configured to store an x-ray image comprising the one or more partial exposed image frames and the one or more null image frames.

7. The x-ray detector of claim 6, wherein the buffer is configured to store an x-ray image comprising the one or more partial exposed image frames, the one or more null image frames, and the one or more dark frames.

8. The x-ray detector of claim 5, wherein the acquisition control and image processing circuit is further programmed to combine the one or more partial exposed image frames and the one or more null image frames.

9. The x-ray detector of claim 8, wherein the acquisition control and image processing circuit is further programmed to combine the one or more partial exposed image frames, the one or more null image frames, and the one or more dark frames.

10. The x-ray detector of claim 5, wherein the acquisition control and image processing circuit is further programmed to determine if an extraneous signal is present in any of the plurality of electrically-chargeable photosensitive cells by comparing the one or more null image frames to a threshold.

11. The x-ray detector of claim 1, further comprising controllable row selecting switches to connect the electric circuits to electrically-chargeable photosensitive cells of the plurality of electrically-chargeable photosensitive cells of each column to provide the one or more readouts of charge contained in the plurality of electrically-chargeable photosensitive cells.

12. The x-ray detector of claim 11, wherein the controllable row-selecting switches being configured to perform the one or more readouts of charge contained in the plurality of electrically-chargeable photosensitive cells one row at a time.

13. The x-ray detector of claim 11, wherein the acquisition control and image processing circuit is further programmed to acquire the one or more partial exposed image frames by exposing the plurality of electrically-chargeable photosensitive cells to radiographic radiation during the one or more readouts of charge contained in the plurality of electrically-chargeable photosensitive cells and to acquire the one or more dark frames by not exposing the plurality of electrically-chargeable photosensitive cells to radiographic radiation during the one or more readouts of charge contained in the plurality of electrically-chargeable photosensitive cells.

14. A method comprising:
   image scanning a two dimensional array of pixels to determine a first image data frame therein;
   exposing the two dimensional array of pixels to a pulse of radiographic radiation after starting, and during the step of, image scanning;
   after the step of exposing, image rescanning the two dimensional array of pixels to determine a second image data frame therein; and
   combining the determined first image data frame with the determined second image data frame of the two dimensional array of pixels.

15. The method of claim 14, further comprising:
   recording in electronic memory the determined first image data frame of the two dimensional array of pixels; and
   recording in the electronic memory the determined second image data frame of the two dimensional array of pixels, and
   wherein the step of combining includes combining the recorded first image data frame with the recorded second image data frame of the two dimensional array of pixels.

16. The method of claim 14, further comprising:
null scanning the two dimensional array of pixels to determine a null image data frame therein,
wherein the step of image scanning includes reading out a portion of the two dimensional array of pixels while a corresponding gate line is turned on, and
wherein the step of null scanning includes reading out a portion of the two dimensional array of pixels while a corresponding gate line is turned off.

17. The method of claim 16, further comprising subtracting the determined null image data frame in the two dimensional array of pixels from the combined first image data frame and second image data frame in the two dimensional array of pixels.

18. The method of claim 16, wherein the step of image scanning the two dimensional array of pixels comprises sequentially image scanning each row of the two dimensional array of pixels individually, and wherein the step of null scanning the two dimensional array of pixels comprises sequentially null scanning each row of the two dimensional array of pixels individually immediately after image scanning each row of the two dimensional array of pixels individually.

19. The method of claim 16, further comprising:
dark scanning the two dimensional array of pixels to determine a dark image data frame therein; and
combining the determined dark image data frame in the two dimensional array of pixels, the determined null image data frame in the two dimensional array of pixels, and the combined first image data frame and second image data frame in the two dimensional array of pixels,
wherein the step of dark scanning includes not exposing the two dimensional array of pixels to any radiographic radiation during the step of dark scanning.

20. The method of claim 14, further comprising:
dark scanning the two dimensional array of pixels to determine a dark image data frame therein; and
combining the determined dark image data frame in the two dimensional array of pixels with the combined first image data frame and second image data frame in the two dimensional array of pixels,
wherein the step of dark scanning includes not exposing the two dimensional array of pixels to any radiographic radiation during the step of dark scanning.

* * * * *